United States Patent
Hannemann et al.

(10) Patent No.: US 10,863,957 B2
(45) Date of Patent: *Dec. 15, 2020

(54) CONTROL OF THE POSITIONING OF A SCANNING REGION OF A MEDICAL IMAGING SYSTEM

(71) Applicant: Siemens Healthcare GmbH, Erlangen (DE)

(72) Inventors: Thilo Hannemann, Erlangen (DE); Soren Kuhrt, Erlangen (DE); Johann Uebler, Nuremberg (DE); Bernhard Weyermann, Hoechstadt (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 782 days.

This patent is subject to a terminal disclaimer.

(21) Appl. No.: 15/501,016

(22) PCT Filed: Aug. 13, 2015

(86) PCT No.: PCT/EP2015/068627
§ 371 (c)(1),
(2) Date: Feb. 1, 2017

(87) PCT Pub. No.: WO2016/026758
PCT Pub. Date: Feb. 25, 2016

(65) Prior Publication Data
US 2017/0224298 A1    Aug. 10, 2017

(30) Foreign Application Priority Data

Aug. 22, 2014    (DE) .................. 10 2014 216 718

(51) Int. Cl.
*A61B 6/00*    (2006.01)
*A61B 5/00*    (2006.01)
(Continued)

(52) U.S. Cl.
CPC ............ *A61B 6/469* (2013.01); *A61B 5/0075* (2013.01); *A61B 5/0077* (2013.01); *A61B 5/744* (2013.01);
(Continued)

(58) Field of Classification Search
CPC ....... A61B 5/00; A61B 5/0059; A61B 5/0062; A61B 5/0064; A61B 5/0075;
(Continued)

(56) References Cited

U.S. PATENT DOCUMENTS 6,346,124 B1 * 2/2002 Geiser .................. G06T 7/0012
600/450
8,059,873 B2 * 11/2011 De Bliek .................. G06T 7/12
128/922
(Continued)

FOREIGN PATENT DOCUMENTS

CN    1476812 A    2/2004
CN    101023890 A    8/2007
(Continued)

OTHER PUBLICATIONS

Chinese Office Action and English translation thereof dated Feb. 1, 2019.
(Continued)

*Primary Examiner* — Anastasia Midkiff
(74) *Attorney, Agent, or Firm* — Harness, Dickey & Pierce, P.L.C.

(57) ABSTRACT

A method and a device are disclosed for controlling a scanning region of a medical imaging system for subsequent recording of a region of interest of an examination object. Depth image data of the examination object are captured. 2-D image data of at least one 2-D image of the examination object are created and the 2-D image is displayed. The 2-D image data and the depth image data of the examination
(Continued)

object are registered to each other at least in some regions. By using the 2-D image, at least one limit position of the scanning region is then determined. Finally, on the basis of the depth image data and the limit position in the 2-D image of the examination object, a limit contour line extending through the limit position is determined and displayed such that the limit contour line is superimposed on the 2-D image of the examination object.

21 Claims, 3 Drawing Sheets

(51) Int. Cl.
*A61B 6/03* (2006.01)
*A61B 6/04* (2006.01)

(52) U.S. Cl.
CPC ............ *A61B 6/032* (2013.01); *A61B 6/0492* (2013.01); *A61B 6/463* (2013.01); *A61B 6/466* (2013.01); *A61B 6/488* (2013.01); *A61B 6/547* (2013.01)

(58) Field of Classification Search
CPC ..... A61B 5/0077; A61B 5/0082; A61B 5/103; A61B 5/1007; A61B 5/1079; A61B 5/74; A61B 5/742; A61B 5/7245; A61B 5/743; A61B 34/00; A61B 34/10; A61B 2034/101; A61B 2034/105; A61B 2034/107; A61B 6/00; A61B 6/02; A61B 6/03; A61B 6/032; A61B 6/04; A61B 6/0492; A61B 6/08; A61B 6/46; A61B 6/461; A61B 6/463; A61B 6/467; A61B 6/469; A61B 6/52; A61B 6/5211; G06T 3/00; G06T 3/005; G06T 7/0012; G06T 7/0014; G06T 7/10; G06T 7/149; G06T 7/174; G06T 7/194; G06T 7/30; G06T 7/32; G06T 7/33; G06T 7/337; G06T 7/50; G06T 7/521; G06T 7/55; G06T 7/564; G06T 7/586; G06T 7/97; G06T 2207/10; G06T 2207/10048; G06T 2207/20092; G06T 2207/20096; G06T 2207/20104; G06T 2207/20112; G06T 2207/20116; G06T 2207/20212; G06T 2207/30; G06T 2207/30004; G06T 2207/30196; A61N 5/10; A61N 5/1048; A61N 5/1049; A61N 2005/105; A61N 2005/1056
See application file for complete search history.

(56) References Cited

U.S. PATENT DOCUMENTS

| | | | |
|---|---|---|---|
| 2004/0081341 A1 | 4/2004 | Cherek et al. | |
| 2007/0172102 A1 | 7/2007 | Hempel | |
| 2012/0294504 A1 | 11/2012 | Kyriakon | |
| 2014/0184749 A1* | 7/2014 | Hilliges | G01S 17/89 348/47 |
| 2015/0103969 A1* | 4/2015 | Flohr | A61B 6/032 378/4 |
| 2015/0104092 A1* | 4/2015 | Flohr | G06K 9/4604 382/131 |
| 2015/0182191 A1* | 7/2015 | Caluser | A61B 8/5246 600/440 |
| 2016/0358333 A1* | 12/2016 | Lee | G06T 7/0012 |
| 2017/0200317 A1* | 7/2017 | Hannemann | G06T 7/13 |
| 2017/0224298 A1 | 8/2017 | Hannemann et al. | |

FOREIGN PATENT DOCUMENTS

| | | |
|---|---|---|
| CN | 102525525 A | 7/2012 |
| DE | 10232676 A1 | 1/2004 |
| DE | 102006001850 A1 | 8/2007 |
| DE | 102007017794 B3 | 12/2008 |
| DE | 102011075904 A1 | 11/2012 |
| DE | 102012201798 A1 | 8/2013 |
| DE | 102012214513 A1 | 2/2014 |
| EP | 1382300 A1 | 1/2004 |
| EP | 2684522 A1 | 1/2014 |
| WO | WO 2014033614 A1 | 3/2014 |
| WO | WO 2016026758 A1 | 2/2016 |

OTHER PUBLICATIONS

Sedlmaier Martin et al., "Kontaktlose Oberflächenvermessung zur Topogramm-Optimierung"; 2013.
Ismail M et al; "3D-Guided CT Reconstruction using Time-Of-Flight Camera"; Proc. of SPIE; vol. 7964; pp. 796420-1-798429-11; 2011.
German Office Action dated May 29, 2015.
International Search Report and Written Opinion dated Nov. 17, 2015.
Office Action for Chinese Patent Application No. 201560045063.1 dated Apr. 26, 2020 and English translation thereof.

* cited by examiner

CONTROL OF THE POSITIONING OF A SCANNING REGION OF A MEDICAL IMAGING SYSTEM

PRIORITY STATEMENT

This application is the national phase under 35 U.S.C. § 371 of PCT International Application No. PCT/EP2015/068627 which has an International filing date of Aug. 13, 2015, which designated the United States of America and which claims priority to German patent application number DE 102014216718.3 filed Aug. 22, 2014, the entire contents of which are hereby incorporated herein by reference.

FIELD

An embodiment of the invention relates to a method and a device for controlling the positioning or selection of a scanning region of a medical imaging system, in particular a radiological imaging system, such as a computed-tomography system (CT) or a C-arm X-ray device.

BACKGROUND

Prior to imaging scanning, as a rule it is first necessary to define a so-called "scanning region" (which can also be called a field of view=FoV), i.e. the region from which image data is recorded or raw data is acquired during a "scanning process" in order to generate the desired image data therefrom. In many cases, the scanning region is defined with the aid of at least one topogram generated in a simple preliminary scan. This topogram (also called a positioning image or overview image) is for example a simple projection of an examination region of the examination object (for example a patient's thorax) containing the region of interest (for example, the heart and lungs) for the "diagnostic" imaging from which the image data that can be used for later diagnosis is generated in order in this way to be able automatically or manually to perform precise positioning of the region of interest. In the case of a CT system, a topogram is, for example, generally a simple X-ray projection, which can be generated in a scanning process with an X-ray source fixed with respect to the angle of rotation. This is followed by the actual scanning process for the generation of the three-dimensional image data or the slice images in a serial or spiral scan. The following assumes, without limiting generality, that the examination object is a patient, most usually a human. However, the patient can in principle also be an animal. Hence, in the following the two terms "examination object" and "patient" are used synonymously.

In particular with CT devices, it is necessary to avoid exposing a patient to unnecessary radiation. Therefore, regardless of whether the requirement is first only to determine a scanning region for the recording of the topogram or to determine a scanning region directly for the diagnostic imaging, said region should be selected as small as possible. Nevertheless, it is obviously also necessary for the region of interest (ROI) to be fully covered. In addition, the user or operator of the system must be able to identify precisely which anatomical regions of the patient are to be captured by the current setting, i.e. whether the ROI is located entirely in the scanning region. A faulty setting results in the patient being exposed to unnecessary radiation and, to be precise, both in cases when the scanning region is significantly larger than the ROI and in cases when the scanning region is smaller than the ROI, since in the latter case the ROI is not depicted sufficiently and it is therefore necessary to repeat the scanning process.

At present, positioning of a scanning region can take place by the manual selection of a start line and an end line of the scanning region, which are marked by means of a light sighting device with laser marking lines on a patient or examination object lying on an object table (patient examination table) of the imaging system that can be moved in the longitudinal direction (z-direction) relative to a scanner (for example the gantry of a CT system). In this case, the longitudinal axis of the patient is as a rule parallel to the longitudinal direction of the object table and, at the same time, the object table is typically located outside the scanner. In this case, the start and end line extend in the width direction (x-direction) of the object table thus defining the scanning region in the longitudinal direction of the patient. However, setting by means of the laser sighting device is relatively time-consuming. It is also necessary to ensure that the patient does not find the laser marking lines distressing.

The user only sets the scanning region only in the direction of the table feed. The start and end points of the scanning region for capturing image data from a three-dimensional volume, for example in the case of a CT scan, corresponds to a slice in the image reconstruction, which is represented by a plane in the space generally perpendicular to the direction of movement of the object table during the scan.

It would be advantageous for the user also to be able to identify the dimensions of the scanning region perpendicular to the table feed even if they cannot be adjusted, since they are determined by the construction of the CT scanner—in particular the distance between the X-ray source and detector and the size of the detector. Here, it is necessary to differentiate between the recording of a topogram and the recording of the actual CT scan.

The recording of a topogram corresponds (in the direction perpendicular to the table feed) to the recording of a conventional X-ray recording. The optical analog is the pinhole camera, wherein the aperture of the camera is located in the focus of the X-ray source. The field of vision is limited by the size of the detector. While, in the direction of the table feed, the scanning region is limited by two planes, which are parallel to one another, in the direction perpendicular thereto, it is limited by two intersecting planes. Their line of intersection is parallel to the table feed direction and contains the focus of the X-ray tube. The aperture angle of the two planes is defined in that they in each case intersect opposite ends of the detector.

During the recording of the actual CT scan, the X-ray source and detector are rotated about the patient. The cut-set of all topogram scanning regions produces a circular region, which is known as the "field of view" (FoV). A display region different from the FoV is generated algorithmically during the tomography reconstruction. In this case, it is very advantageous, if possible, for all relevant objects to be located inside the FoV since objects outside the FoV can only be reconstructed very imprecisely and generate image artifacts which could also affect objects inside the FoV.

It would, in principle, be possible to record an image of the patient lying on the object table with a camera and depict it on a display at a control terminal or the like of the system, wherein then the current start and end positions of the scanning region can be depicted in the image by superimposed lines. However, unfortunately, the depiction a start and end point of the scanning region by means of lines in the image is not correct. Namely, the formation of the image in the camera can be approximated by a pinhole camera model since all sight beams intersect each other in one point—the aperture plate. Each pixel (i.e. image point) of the camera is assigned a sight beam containing those points in space that could potentially be depicted on this pixel. Each pixel in the camera's image corresponds to the gray or color value of the object at the point where the sight beam extending through the pixel and the aperture plate intersects the object. Therefore, the sight beams of all pixels form a divergent sight beam bundle.

This does not correspond to the imaging geometry of the CT scan. As explained above, in the direction of movement of the object, the scanning region is limited by two parallel planes. The pixels in the camera's image corresponding to this plane only form a straight line under quite specific conditions, namely in the case of a telecentric image, i.e. a (virtually) infinite distance between the camera and the object in the pinhole camera model, or when the camera's "aperture plate" is actually located in the spatial plane to be depicted, i.e. directly above the start or end position. A telecentric image is structurally difficult to implement since the camera's entrance optics must be at least the size of the object. On the other hand, a camera located in the spatial plane to be displayed can obviously only be implemented for precisely one selection of the spatial plane and therefore in principle is not simultaneously suitable for the start and end position.

Due to the geometry of the structure, in particular the fact that the camera requires a large aperture angle in order to be able to capture the whole patient from its position, for example on the ceiling of the room or on the top of a gantry of the CT system, the resulting error is not insignificant and hence precise setting of the scanning region is no longer possible.

With a topogram, there is a very similar problem perpendicular to the direction of movement of the object with the difference that the limiting planes are not parallel, but intersect one another. In the camera's image, the lateral limit would only be correctly depicted as a line when the camera's aperture is located on the line of intersection of the two limiting planes. This is impractical since this would require the camera to be located very closely above the patient.

In the case of the recording of a CT scan, as explained above, the FoV is defined by a cylindrical volume. This has no equivalent in the pinhole camera model but has to be depicted by means of a calculation in the three-dimensional space.

SUMMARY

At least one embodiment of the present application provides a method and/or a device for positioning a scanning region of a medical imaging system in order enable a scanning region to be set as precisely and quickly as possible with the lowest possible inconvenience or distress to a patient.

At least one embodiment of the present application is directed to a method. At least one embodiment of the present application is directed to device.

A method of at least one embodiment is disclosed for controlling the positioning of a scanning region of a medical imaging system for subsequent recording of a region of interest of an examination object, wherein depth image data of the examination object is captured,
optionally, 2D image data of at least one 2D image of the examination object is created,
and wherein the 2D image data and the depth image data of the examination object are registered to each other at least in some regions, the 2D image is displayed and, by using the 2D image at least one limit position of the scanning region is determined and a limit contour line extending through the limit position is determined on the basis of the depth image data of the examination object and the limit position in the 2D image of the examination object, said limit contour line being displayed superimposed on the 2D image of the examination object, or wherein a three-dimensional avatar of the examination object is created and displayed on the basis of the depth image data of the examination object, preferably using the 2D image data of the examination object, the display of the avatar is used to define limit positions, preferably limit lines, of the scanning region.

In a second embodiment of the method according to the invention, an individual three-dimensional avatar for the examination object created is created on the basis of the depth image data of the examination object, and—in particular instead of the 2D image in the first variant—visualized optically for the operator of the system, for example on a display unit, preferably a touch-screen monitor, in a telecentrically correct manner. As will be explained below, the display of the avatar can then define limit positions, preferably limit lines, particularly preferably limit contour lines (i.e. limit lines adapted to the contours of the avatar) which limit or define the scanning region.

A device according to at least one embodiment of the invention (in at least one embodiment, for carrying out an embodiment of the method) comprises at least:

- a depth-image-data sensor, which captures depth image data of the examination object captured.
- optionally (when using the first method variant, obligatorily) a 2D camera, wherein this can be a 2D photographic camera or 2D video camera, which creates 2D image data for a 2D image of the examination object.
- a registration unit, which is embodied, to register the 2D image data and the depth image data as described above to each other at least in some regions and/or an avatar-creating unit, which is embodied to create a three-dimensional avatar of the examination object on the basis of the depth image data, preferably using the 2D image data of the examination object. The registration unit and/or the avatar-creating unit can, for example, be integrated in a control unit of the medical imaging system or in a camera unit, for example in the form of software, as will be explained below.
- an image-display unit, for example the display unit, to display the 2D image and/or the avatar of the examination object.
- a limit-positioning-capturing unit, which is embodied to capture at least one limit position of the scanning region by using the 2D image and/or avatar, as was described in connection with the method according to the invention.
- at least, when the device is to be used carry out the first variant of the method, a limit-contour-line-determining unit, which is embodied to determine a limit contour line of the scanning region extending through the limit position on the basis of the depth image data and the limit position in the 2D image, said limit contour line extending on a surface of the examination object, preferably such that the limit contour line corresponds to a geometric course of a light or laser marking projected onto the patient. This limit-contour-line-determining unit can also, for example, be implemented as a software module, in particular in the control unit of the medical imaging system. The device according to the invention is then also embodied such that the limit contour line of the scanning region determined is displayed superimposed on the 2D image in the image-display unit.

At least one embodiment is directed to a medical imaging system, in particular a computed tomography device, containing at least one embodiment of the device.

The claims and the following description contain particularly advantageous developments and embodiments of the invention, wherein in particular the claims of one category can be developed similarly to the dependent claims of another claim category. It is also possible for features of different variants and embodiments to be combined.

BRIEF DESCRIPTION OF THE DRAWINGS

The invention is described again in more detail below with reference to the attached figures with reference to example embodiments. In this case, identical components are given identical reference characters in the different figures. The figures are generally not to scale, in which.

DETAILED DESCRIPTION OF THE EXAMPLE EMBODIMENTS

Figure 1:
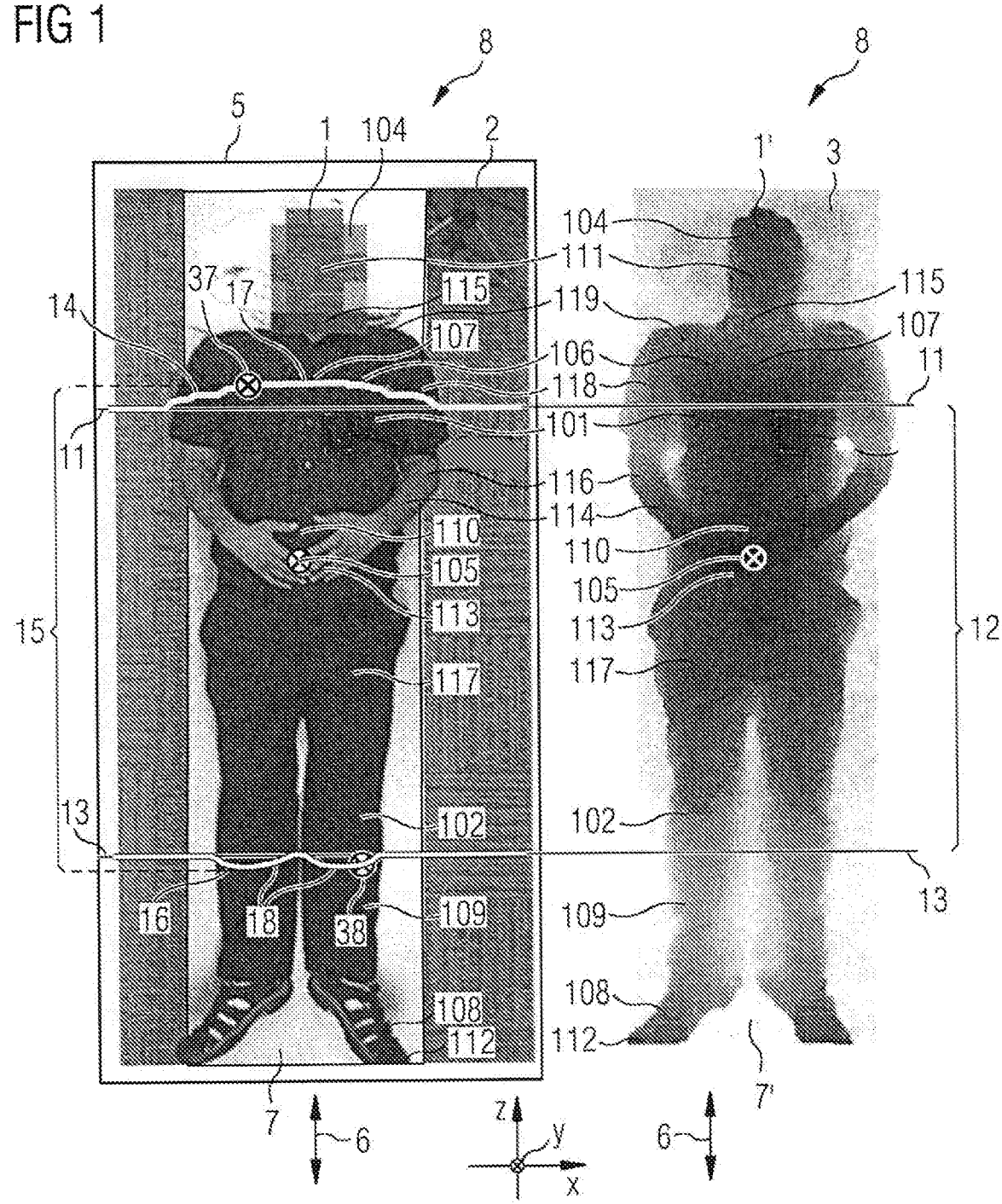
FIG. 1 shows two images recorded from the same perspective and simultaneously of a patient, a 2D image on the left and a depth image on the right.

One aspect of the method according to at least one embodiment of the application is always the capturing of depth image data of the examination object.

In addition, optionally 2D image data of at least one two-dimensional image (2D image) of the examination object is created.

In order to utilize this data, depth image data of the examination object on the one hand and optional 2D image data on the other, there are substantially two basic variants of the method according to the invention:

In a first embodiment, the 2D image is visualized for the operator of the system, for example on a display unit, preferably a touch-screen monitor. Therefore, the capture of the 2D image data is obligatory for this variant.

In this context, at least in some regions (i.e. for example at least in one region of the assumed limit contour lines of the scanning region which are generated later and/or at specific easily identifiable anatomical landmarks) the 2D image data and the depth image data of the examination object are registered to each other. In this case, the depth image data is registered to the 2D image data so that the actual 2D image remains as unchanged or undistorted as possible. However, in principle, the 2D image data could also be registered to the depth image data if this were to be desired in a specific application. Similarly, it would also be possible for there to be a mutual partial registration of the depth image data and the 2D image data to each other so that the 2D image may be displayed as slightly distorted but, if possible, not in the scanning region or examination region and in particular not in the actual region of interest of the examination object. Therefore, a display of the start and end lines of the scanning region that is correct with respect to physical geometry or enhanced does not necessitate any distortion of the patient image. Nevertheless, the patient image can still be distorted for other reasons, for example in order to correct aberrations due to the optics.

The 2D images displayed are used to determine at least one limit position in the form of one or more points or one or more lines of the scanning region.

As will be described below, to this end, in one example embodiment of the invention, the operator could tap a touch-screen monitor at least once for the limit contour line starting the subsequent scanning process, hereinafter also referred to as the "start line" of the scanning region, and once for the limit contour line ending the subsequent scanning process, hereinafter referred to as the "end line" of the scanning region. This enables the limit positions of a start line and an end line of the scanning region to be defined at the points of contact on the monitor. The subsequently determined, in particular calculated, course of the limits of the scanning region which is visualized on the monitor then passes through these points.

Then, a limit contour line extending through the limit position is determined on the basis of the depth image data of the examination object (registered to the 2D image data) and the limit position in the 2D image of the examination object, said limit contour line extending (virtually) on a surface, i.e. the outer contours, of the examination object. This limit contour line is visualized superimposed on the 2D image of the examination object, for example on said display unit.

In addition, the information on the size of the scanning region can be superimposed perpendicular to the table feed. This can, for example, take place in the form of a lateral limiting line. Alternatively, it is also conceivable, similarly to the exposure warning in a digital camera, for the region of the patient that is not subsequently to be visualized in the topogram/CT scan to be highlighted in color or by flashing.

In a second embodiment of the method according to the invention, an individual three-dimensional avatar for the examination object created is created on the basis of the depth image data of the examination object, and—in particular instead of the 2D image in the first variant—visualized optically for the operator of the system, for example on a display unit, preferably a touch-screen monitor, in a telecentrically correct manner. As will be explained below, the display of the avatar can then define limit positions, preferably limit lines, particularly preferably limit contour lines (i.e. limit lines adapted to the contours of the avatar) which limit or define the scanning region.

Those parts of the avatar corresponding to the body parts of the patient which are subsequently not to be entirely contained in the topogram/CT scan can be marked perpendicular to the table feed direction.

In this context, an avatar should be understood to be an artificial virtual image or a graphical representative of the patient. This avatar can be calculated individually on the basis of the known patient data. Preferably, at least a part, particularly preferably all, of the following information will be used for the creation of the avatar:

anatomical landmarks for avatar scaling (leg length, arm length, thorax-abdomen), gender, ethnic features,
body outline (shape),
body volume,
patient position,
if known, patient weight.

The most important parts of this information, such as anatomical landmarks, body outline, body volume and patient position can be determined from the depth image data determined. Some types of information, such as age and gender, can also be retrieved from an electronic patient file. However, at least partially, a part of this information can also be obtained particularly simply with the aid of the (optionally generated) 2D image data of the examination object. This applies in particular to further anatomical landmarks, ethnic features (which are generally identifiable from the face), body outline (at least viewed from one side) and, to some extent, the patient position. Therefore, preferably, further, in particular biometric, data (such as, for example, skin color) of the examination object is determined on the basis of the 2D image data and used for the individual generation of the avatar for the examination object.

A device according to at least one embodiment of the invention (in at least one embodiment, for carrying out the method) comprises at least:
- a depth-image-data sensor, which captures depth image data of the examination object captured.
  - optionally (when using the first method variant, obligatorily) a 2D camera, wherein this can be a 2D photographic camera or 2D video camera, which creates 2D image data for a 2D image of the examination object.
  - a registration unit, which is embodied, to register the 2D image data and the depth image data as described above to each other at least in some regions and/or an avatar-creating unit, which is embodied to create a three-dimensional avatar of the examination object on the basis of the depth image data, preferably using the 2D image data of the examination object. The registration unit and/or the avatar-creating unit can, for example, be integrated in a control unit of the medical imaging system or in a camera unit, for example in the form of software, as will be explained below.
  - an image-display unit, for example the display unit, to display the 2D image and/or the avatar of the examination object.
  - a limit-positioning-capturing unit, which is embodied to capture at least one limit position of the scanning region by using the 2D image and/or avatar, as was described in connection with the method according to the invention.
  - at least, when the device is to be used carry out the first variant of the method, a limit-contour-line-determining unit, which is embodied to determine a limit contour line of the scanning region extending through the limit position on the basis of the depth image data and the limit position in the 2D image, said limit contour line extending on a surface of the examination object, preferably such that the limit contour line corresponds to a geometric course of a light or laser marking projected onto the patient. This limit-contour-line-determining unit can also, for example, be implemented as a software module, in particular in the control unit of the medical imaging system. The device according to the invention is then also embodied such that the limit contour line of the scanning region determined is displayed superimposed on the 2D image in the image-display unit.

Optionally, the device can also in each case comprise a limit-positioning-determining unit, which can, for example, be arranged in the control unit of the imaging system, in particular also in the limit-positioning-capturing unit or the display unit. This limit-positioning-determining unit can determine the actual limit position of the scanning region on the basis of the position data of the limit position captured before in the limit-positioning-capturing unit and optionally store this in a memory. In this case, the captured position data is only sensor data on a screen of the image-display unit. Contrary to this, the limit position data determined are optionally further processed, in particular to correct errors, for example resolution errors due to a finger width or unwanted multiple entries with several fingers in a very short time interval.

Furthermore, an embodiment of the present invention comprises a medical imaging system, in particular a CT system containing the device according to an embodiment of the invention.

The first variant according to an embodiment of the invention with the use of the 3D-depth image data for the perspectively correct display of the scanning region in that limit contour lines that have been corrected by computer are generated so that they preferably correspond geometrically to a light or laser marking projected virtually onto the patient without any distortion to the 2D patient image inter alia achieves the following advantages:
- a very precise selection of the scanning region taking into account the current position of the patient is possible.
- there is "compatibility" with the light sighting device planning since the display of the graphical positioning line is similar to the light sighting device. In this context, "compatible" means that a user or operator should not experience any difficulties when using the invention, since this results in start and end lines that are comparatively similar to the currently most frequently used method, namely the positioning of a scanning region with laser marking.
- each "orientation point" selected by the user in the patient image can be selected for the graphical position planning. "Orientation points" are specific points on the patient which the user uses for orientation in order to define the scanning region (for example elbow, chin, belt buckle, etc.). "Graphical position planning" is a positioning of a scanning region of an examination device by means of the selection at least one start line and at least one end line of the scanning region.
- computer-generated position planning is displayed correctly in a way understandable to the user (for example on the basis of scan protocol information on the examination region and anatomical landmarks (biometric data) or anatomical models).
- more precise planning without exposing the patient to radiation is possible.
- the depiction of the patient image on the display is as realistic as possible and appealing since no distorting image operations are required on the patient image.
- cumbersome movement of the table back and forth is no longer necessary for the planning.

The second variant according to an embodiment of the invention for the use or display of an avatar inter alia achieves the following advantages:
- each orientation point selected by the operator in the image with the display of the avatar can be selected for the graphical position planning. This enables the precise selection of the scanning region taking into account current position of the patient possible without perspective distortions.

the avatar is an appealing display without any missing information or distortions, i.e. here, once again no distorting image operations are required on the patient image.

disruptive objects, for example infusion bottles or monitoring devices that would be visible on a live image can be masked out.

the avatar is an (extensively) anonymized view of the patient, thus increasing data security. The patient does not have to worry about camera images being stored in the system.

a patient lying partially or completely naked on the table can always be represented appropriately by the avatar.

any "fears of contact" on the part of the operator if required to work "with the fingers" on a real-time image on a touch-screen are avoided.

the avatar can be displayed in different positions, in particular a view of the patient from the side is possible—this can, for example, be of interest for setting a scan height.

Furthermore, a combination of the variants of embodiments is also possible in order to combine particularly interesting advantages of the variants of embodiments for the specific application the operator's preferences in each case. For example, as with the first variant, it is also possible for limit contour lines to be created and superimposed on the avatar displayed with the second variant. In a particularly preferred combined variant, the 2D image data is, for example, used to provide the avatar with a real face. I.e. only the patient's body is displayed as an avatar and the face is, for example, a live image.

In addition, with all variants and embodiments, it is also possible for the total stress for the patient, possibly in particular the radiation exposure, but also the duration of the examination, to be minimized since the user finds the method and the device simpler, quicker and precise to handle and the time spent by the patient in the gantry is minimized. In addition, the operator and manufacturer find the device economical to produce, operate, maintain and repair.

The claims and the following description contain particularly advantageous developments and embodiments of the invention, wherein in particular the claims of one category can be developed similarly to the dependent claims of another claim category. It is also possible for features of different variants and embodiments to be combined.

The position data of the limit contour line of the scanning region can be determined either by calculation by means of algorithms or by reading out tabular values from an internal or external database. Furthermore, the position data of the limit contour line of the scanning region can also be determined from a combination of the two methods. Here, preference is given to determination with the aid of a calculation specification that assigns the position data of the limit contour line to a geometric course of a light or laser marking of a "virtual interface" extending perpendicular to the surface of the object table projected virtually onto the patient since these are familiar to the majority of operators from the prior art.

The limit line or limit contour line of the scanning region is preferably displayed in the form of a continuous or repeatedly interrupted start line or end line. The light or laser markings of these lines projected virtually onto the patient then so-to-speak extend on the surface of the patient in a "virtual cutting plane" extending perpendicular to the surface of the object table and longitudinal axis of the patient. Quite particularly preferably, as mentioned above, a start line and an end line are created, between which the scanning region is defined. The start line or end line are displayed at least within the lateral outer contours of the patient (i.e. at least on the patient). However, for purposes of simplification, the start line or end line are preferably depicted over the entire 2D image of the patient with the object table. In this case, the limit (contour) lines preferably extend transversely to a direction of movement of the object table on which the examination object is arranged.

In one preferred embodiment of the invention, the 2D image data of the examination object is created with light in the wavelength range, for example between 380 nm and 780 nm. Particularly preferably, the 2D image is visualized as a color image. Alternatively, a display as a black-and-white image with a plurality (for example 256) of grayscale values is useful. However, the 2D image data can also be recorded outside the visible wavelength range, for example in the infrared wavelength range between 780 nm and 1000 nm.

In a further preferred embodiment of the invention, the depth image data of the examination object is created in the infrared wavelength range, for example between 780 nm and 1000 nm, created thus enabling a particularly robust determination of the depth image data. However, it is also possible for other wavelength ranges to be used for the determination of the depth image data.

The 2D image data or the 2D image can be a still image or sequence of images with, for example, 12, 24, 50 or 60 images per second. The same applies to the depth image data, which can also be still image data or sequential image data.

Preferably in each case a 2D image and the associated depth image data of the examination object, with which the registration is to be performed, are created simultaneously or quasi-simultaneously (i.e. at approximately the same time with only a small time interval, for example of max. 1 s or less). This ensures that unwanted movements by the patient are not reflected in the image data resulting in the faulty registration of the 2D image data and the depth image data of the examination object to each other.

In one particularly preferred embodiment of the invention, the 2D image data and the depth image data of the examination object are created from the same or almost the same perspective created. For example, the optical axes of the 2D image camera and the depth image sensor preferably have a maximum deviation of approximately ±1% of a maximum dimension of the scanning region. If, for example, the scanning region has a length of 0.5 m in the z-direction, the maximum deviation of the optical axes of the 2D image camera and the depth image sensor is approximately 5 mm. A preferred distance between the camera-unit and the examination object or its geometric center is for example 2 m±50%, i.e. between 1 m and 3 m. This enables the risk of the depth image data of the examination object containing faulty data due to self-shading of the examination object to be reduced. Hence, this enables a complete determination of the scanning region without any possible falsifying interpolations or extrapolations of the depth image data. This makes it simpler to prevent the resolution, and hence the number, of pixels being too low in particular in the depth image data.

To this end, in one preferred embodiment of the invention, the 2D camera and the depth-image-data sensor, a particularly preferably also a registration unit, are combined structurally and logically in a common (i.e. spatially united) camera-unit. In this case, the camera-unit is in particular preferably embodied as a TOF camera ("time Of flight"

camera), for example with a photon mixing detector (PMD) operating by means of time-of-flight methods with optically visible light or infrared light. Such units are relatively inexpensive. Alternatively, the camera can also make the 3D-data available by means of a stereo-image method or by illumination with structured light or a combination thereof. The camera unit can be simply mounted on the ceiling of a room or a frame of the medical imaging system and coupled to a control unit in the system in a signal-conducting manner (wire-bound or wireless).

In one particularly preferred embodiment of the invention, the 2D image data and the depth image data of the examination object are created from a perspective, which is arranged approximately over the geometric center of a planned, prospective scanning region, at least in the z-direction and optionally also in the x-direction. Therefore, the 2D camera and/or the depth-image sensor are correspondingly arranged over the region or can be moved thereto. The result of this is that the scanning region is approximately subdivided into two identical sub-regions, at least in the z-direction and optionally also in the x-direction. As a result, on the one hand, the 2D image is less distorted and, on the other, self-shading of the examination object is reduced and hence the depth image data has a lower amount of faulty data to be corrected, in each case compared to an off-center positioning of the 2D image camera and the depth image sensor. This enables more precise control of the positioning of the scanning region.

Alternatively, in a particularly preferred embodiment the 2D image data and/or the depth image data, are then, at least in the x-direction and optionally also in the z-direction, created from a perspective in a region over the geometric center of a object table on which the examination object is located, i.e. from a perspective approximately over the geometric center of the actual examination object. This is in particular advantageous if a plurality of scanning regions is to be defined during which the examination object is not to be moved relative to a camera unit.

In one particularly preferred embodiment of the invention, the 2D image of the examination object and/or the avatar and the limit lines or limit contour lines of the scanning region are visualized to the operator on a display unit with a image-display unit and line-positioning-capturing unit, in particular a touch-screen monitor (i.e. on a touch-sensitive screen). This enables the operator to change the limit (contour) line of the scanning region particularly simply and intuitively as described below. It is in particular possible for a touch-screen monitor that is already present in a CT system to be used to display the 2D image of the examination object and the limit contour line(s) of the scanning region.

In this case, the line-positioning-capturing unit of the display unit is embodied such that it detects movements of a pointer object (for example an operator's finger movements or stylus movements) in front of or on the display unit. It is then possible to change a limit contour line synchronously with a movement of a pointer object relative to the 2D image displayed on the image-display unit, for example partially distorted or preferably displaced in a direction of movement of an object table. In this case, preferably a limit (contour) line is always activated for a change of this kind, for example the one to which the pointer object is closest. In this case, the change in the position of the limit (contour) line of the scanning region relative to the 2D image of the examination object can advantageously be changed by finger movements of the operator in front of the display unit. In particular, the operator can change the position of the limit (contour) line of the scanning region relative to the 2D image of the examination object intuitively by touching the line-positioning-capturing unit with a finger and moving the fingers on the line-positioning-capturing unit.

In this case, the line-positioning-capturing unit can also be embodied such that it changes the position of the limit contour line of the scanning region relative to the 2D image of the examination object without contact—only by means of mimicking movements and/or gestures of body parts of the operator at the distance from the line-positioning-capturing unit. In this case, a combination of the aforementioned options—with and without contact with the line-positioning-capturing unit—is also possible for changing the position of the limit (contour) line of the scanning region relative to the 2D image of the examination object.

Figure 2:
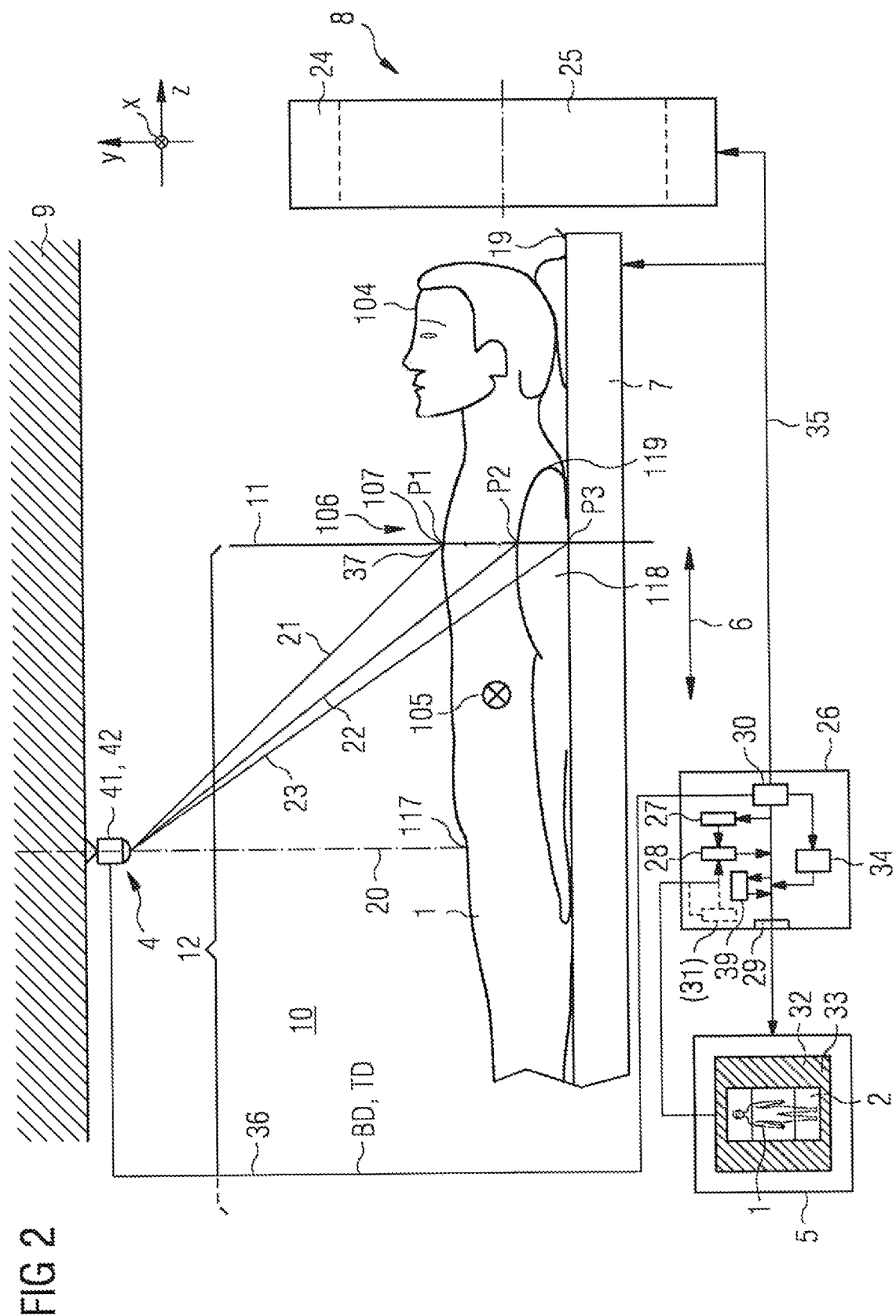
FIG. 2 shows a stylized representation of a side view in the x-direction on the patient from FIG. 1 showing a TOF camera and its sight lines at different heights relative to a bed.

FIG. 1 shows two images of a patient 1, who, as shown in FIG. 2, is lying on an object table 7 (hereinafter "bed" for short) in a conventional CT device 8, which is only shown in a rough sketch here. The bed 7 can be moved in the directions of travel 6 (in the z-direction) and introduced into an examination chamber 25 of a gantry 24 (also called a scanner) of the CT device 8.

Here, the left-hand side of FIG. 1 shows a realistic 2D image 2, for example a photographic or video image, and the right-hand side a depth image 3 of the same patient 1. In the depth image 3, height is associated with a change in grayscale values. Here, the grayscale values are high at high points of the patient 1, for example in the chest region 106, in the abdominal region 110, in the face 111, in the toe region 112 or in places where the hands 113 and arms are placed 114 on the abdominal region 110. The grayscale values are low at low points of the patient 1, for example in the neck region 115, in the elbow region 116 or at the lower legs 109. Both the 2D image data BD of the 2D image 2 and the depth image data of the depth image 3 were created approximately simultaneously by means of a TOF camera 4 from the same perspective.

In a first variant of an embodiment of the invention, only the 2D image 2 is shown on a touch-screen monitor 5. In a real display, the face of the patient is also identifiable and not, as here, pixilated for purposes of anonymization. On the other hand, the depth image 3 is only displayed in FIG. 1 to provide better understanding of an embodiment of the invention.

About 2.5 m above the bed 7, the TOF camera 4 is, for example, arranged on a ceiling 9 of an examination chamber 10 in which the CT device 8 is located. The camera 4 comprises a digital 2D camera 41, a digital depth-image-data sensor 42 and optionally a registration unit 27 (which in this case could be dispensed with in a control unit 26 described below), wherein these three components 41, 42 and 27 are structurally integrated in the housing of the camera 4. The 2D image data BD of the 2D image 2 were recorded with the 2D camera 41 in the visible wavelength range (380-780 nm) and the depth image data TD of the depth image 3 in the infrared wavelength range (780-1000 nm).

In the left-hand 2D image 2, parallel upper and lower "straight" start or end lines 11, 13 with a low line width of, for example, between 1 and 10 millimeters and extending in the width direction (x-direction) are drawn slightly above the chest height 101 and below the knee joints 102 of the patient 1. The actual scanning region extends along the length of the patient 1, i.e. in the z-direction of the examination device. The straight start or end lines 11, 13 of the scanning region 12 are only shown in FIG. 2 for better illustration of the invention. In reality, they are preferably not shown on the monitor 5. Similarly, it is only for better elucidation that the "straight" start lines 11 and end lines 13 in FIG. 1 extend through the right-hand depth image 3 of the patient 1 at the same height in the y-direction.

However, both the "straight" lines 11 and 13 indicate on the monitor 5 limits of the scanning region 12, which as explained below, due to the perspective distortion of the patient 1 generated by the camera, do not correspond in all cases to the real position of the scanning region limits on the patient's body. To this end, in the left-hand 2D image 2 of the patient 1, in each case a corresponding correctly determined start line 14 and end line 16 according to the invention of the actual scanning region 15 are superimposed on the touch-screen monitor 5.

In this case, the upper start line 14 and the lower end line 16 are positioned where an operator has, for example using a finger, touched the touch-screen monitor 5 to set the respective limit line, namely at an upper limit position 37 and a lower limit position 38. The upper start line 14 was guided through the upper limit position 37 and the lower end line 16 through the lower limit position 38.

The correct upper start line 14 and lower end line 16 were determined by calculation on the basis of the depth image data TD registered to the 2D image data BD of the 2D image 2 such that they each correspond as precisely as possible to the geometric course of a light or laser marking projected virtually onto the patient 1 extending in a vertical cutting plane perpendicular to the longitudinal axis of the patient (y-axis).

As is clearly evident in FIG. 1, compared to the straight start line 11, the correct upper start line 14 extends curved in the direction of the head 104 of the patient 1. In this case, the further the start line 14 extends in the width direction (x-direction) of the patient 1 to a geometric center 105 of the patient 1 of the patient 1, the greater the local distance to the straight start line 11 in the z-direction, since, this is where the greatest height of the chest region 106 of the patient 1 (in the y-direction) occurs. Here, there is only a bulge 17 in the upper start line 14, which has a maximum value in the center of the chest on the breastbone 107 of the patient 1.

Compared to the straight end line 13, the correct lower end line 16 extends curved in the direction of the feet 108 of the patient 1 wherein, the further the end line 16 extends in the width direction (x-direction) of the patient 1 to the geometric center 105 of the respective lower leg 109 of the patient 1, the greater the distance in the z-direction to the straight end line 13 since this is where patient 1 has the two greatest heights (in the y-direction) of the lower legs 109. Therefore, here there are two bulges 18 in the lower end line 16, one on each of the two lower legs 109 of the patient 1, with maximum values approximately in the center of the lower legs 109 of the patient 1.

In the region of the bed 7 and of the outer contour of the patient 1, the straight and the correct start lines 11, 14 and end lines 13, 16 coincide because there the heights are zero or only slightly more than zero, with the height of the bed 7 being defined as base "zero" in the height direction (y-direction). Therefore, the cushioned bed 7 in the depth image 3 is virtually uniformly colored white or light gray since all the regions of the bed 7 lie at approximately the same height level and only the cushioning of the bed 7 is slightly deformed by the patient 1 located thereupon.

As a comparison of the straight lines 11, 13 with the correct limit lines 14, 16 reveals, some regions of the patient actually belong to the scanning region 15 which would not be shown as belonging to the scanning region according to the straight lines 11, 13.

Here, the above-defined start line 14 and end lines 16 of the scanning region 15 are selected arbitrarily and can obviously be interchanged so that the scanning process can either progress from the head 104 to the foot 108 of the patient 1 or alternatively from the foot 108 to the head 104 of the patient 1 in the z-direction and, if desired, in both directions with two scans.

Incidentally, solely for reasons of a achieving a clearer depiction of the problem, in the side view in FIG. 2 the camera 4 is not arranged over the geometric center 105 of the patient 1 offset from the center in the direction of the pelvic region 117 of the patient 1 in the z-direction, wherein the optical axis 20 of the camera 4 is perpendicular to this pelvic region 117 of the patient 1. However, the coordinate of the x-direction of the camera 4 approximately corresponds to the x-coordinate of the geometric center 105. On the other hand, FIG. 1 shows the preferred positioning of the camera 4, wherein the optical axis 20 of the camera 4 is arranged in the x-direction and also in the z-direction perpendicular over the geometric center 105 in the abdominal region 110 of the patient 1.

Moreover, in FIG. 2 the start plane 11 only symbolically marks the start of a scanning region 12 intersecting the patient 1 on a longitudinal extension in the z-direction in the chest region 106. No end plane 13, 16 is shown here. Manual positioning of an end or start plane can also be dispensed with wherein these are then automatically superimposed in the z-direction behind the toes 112 or behind the head 104 of the patient 1 so that the patient 1 is scanned from a start plane 11, 14 or to an end plane.

Here, the straight start plane 11 intersects the breastbone 107 and the left upper arm 118 of the patient 1 and the bed 7, wherein to this end three points of intersection P1, P2 and P3 are shown. The point of intersection P1 is assigned to the breastbone 107, the point of intersection P2 to the surface of the left upper arm 118 and the point of intersection P3 to the surface 19 of the bed 7, wherein all three points of intersection P1, P2 and P3 lie in this start plane 11 at the same distance from the camera 4. However, due to the different heights of the points P1, P2 and P3, in the y-direction, these and the assigned sight lines 21, 22, 23 of the camera 4 appear to be at different z-positions on the 2D image 2 and the depth image data TD. The point P1 appears to be further in the direction of the head 104 of the patient 1 than the points P2 and P3, possibly on an extension (in the z-direction) of the shoulder 119 of the patient 1, which in reality lies approximately on the same extension (in the z-direction) as the center of the upper arm 118 of the patient 1. Accordingly, according to the invention, the representation in the 2D image 2 of the correct start plane 14 of the scanning region 15 has to be arched in the direction of the head 104 of the patient 1 on the chest region 106, as described above thus generating the start 14 and end planes 16 of the scanning region 15 shown in FIG. 1.

Figure 3:
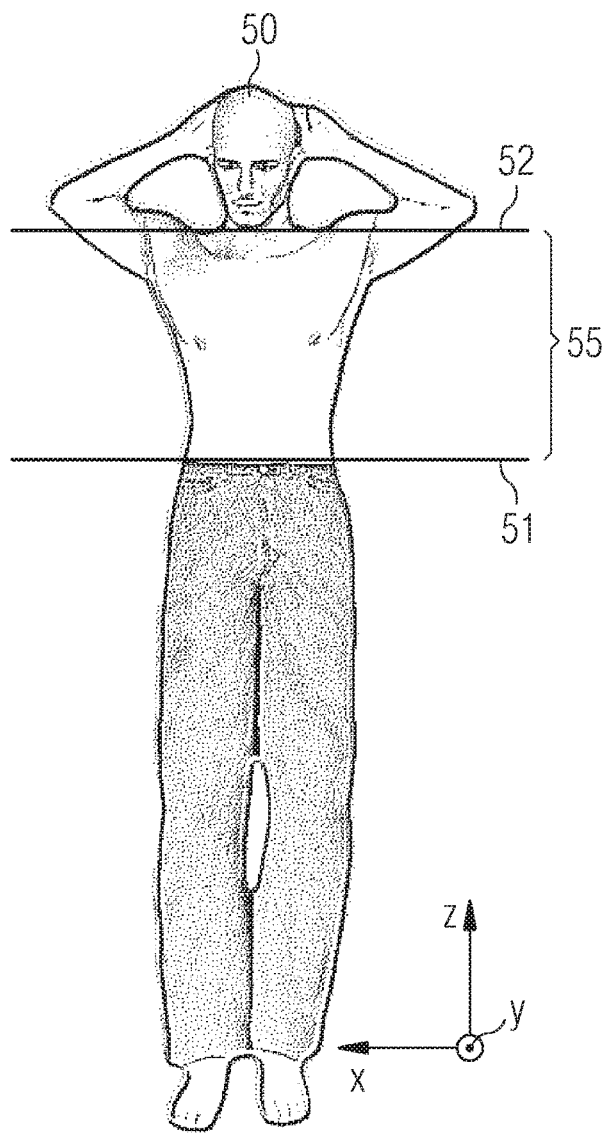
FIG. 3 shows a representation of an avatar created on the basis of the depth image data of a patient from the front.
Figure 4:
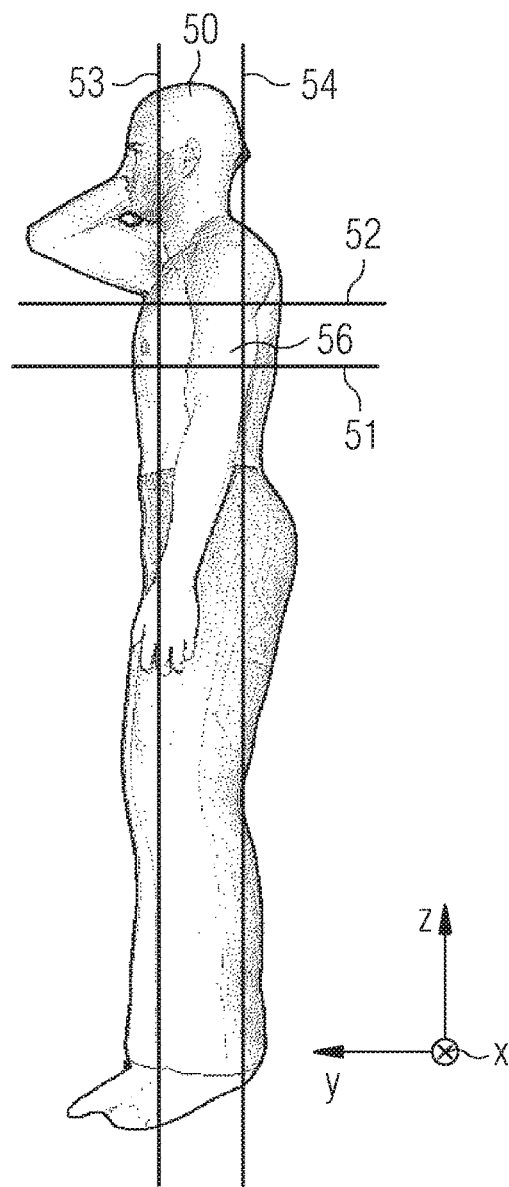
FIG. 4 shows a representation of an avatar of a patient created on the basis of the depth image data from the side.

In a second variant of the method according to an embodiment of the invention, instead of the complete 2D image as shown on the left in FIG. 1, an avatar 50 of the patient 1 is displayed on the touch-screen monitor 5. The display of the avatar 50 can then, as shown in FIGS. 3 and 4, be used to define limit lines 51, 52, 53, 54 limiting the scanning region 55, 56. This avatar 50 is calculated individually for the patient 1 on the basis of the depth image data TD and further known patient data, which can be partially determined on the basis of the 2D image data BD determined. In this case, information on anatomical size ratios, gender, ethnic features, body contour etc. of the patient 1 is used to make the avatar 50 as similar as possible to the patient 1. The operator can then, as will be described below, set any limit lines desired on the avatar 50 shown (for example a start line 51 and an end line 52) (see FIGS. 3 and 4) limiting the scanning region 55, 56 in the z-direction.

In addition to the view from the front as shown in FIG. 3, it is also possible to rotate an avatar 50 of this kind and display it in different positions so that the operator can also obtain a display from the side of the "patient" (avatar) on the monitor 5 (see FIG. 4). In this way, it is possible to define the scan height of the scanning region 56 not only in the z-direction but also in the y-direction.

As with the first variant, in each case, the limit lines 51, 52, 53, 54 can be embodied or displayed as limit contour lines, i.e. in that they are adapted to the contour of the avatar 50 in a cutting plane (for example perpendicular or parallel to the bed 7).

The CT system 8 (also called a CT device) shown in FIG. 2 comprises inter alia the components or assemblies described below. In this case, it is assumed by way of example only that the CT system 8 is embodied such that comprises components suitable for it to be used for all the above-named variants of the method according to the invention.

An annular gantry 24 with a central examination chamber 25, and a bed 7 for a patient 1 that can be moved in the directions of travel 6 into the examination chamber 25 and back.

The gantry 24 comprises at least one (not shown) X-ray source and a X-ray detector arrangement lying opposite thereto relative to the isocenter of the gantry 24, wherein the X-ray source and detector arrangement can be rotated jointly around the isocenter of the gantry 24. Alternatively, it is possible, again with a rotatable X-ray source, for the detector arrangement to be fixed and arranged generally 360° all around the center of the gantry 24. The X-ray source can emit X-rays through a patient 1 lying on the bed 7 in the examination chamber 25 to the detector arrangement, which then detects, spatially resolved, absorption or attenuation of the X-rays on the path through the body of the patient 1 as CT raw data or projection data.

Both the gantry 24 with the X-ray source and the detector arrangement and the movements of the bed 7 can be controlled by means of a processor 30 of a control device 26 via corresponding signal lines 35. The CT raw data captured by means of the detector arrangement are then reconstructed in a CT image processing unit 34 of the control device 26 to form CT image data and routed via an interface 29 to a display unit 5, for example in the form of a touch-screen monitor visualizing a corresponding CT image of the patient 1.

As described, the device according to an embodiment of the invention for controlling the positioning of the geometric course of a scanning region 15 contains a camera-unit 4 in the form of a TOF camera comprising a 2D camera 41 for capturing 2D image data BD for 2D images 2 and a depth-image-data sensor 42 for capturing depth image data TD.

The device according to an embodiment of the invention also comprises a registration unit 27, a limit-contour-line-determining unit 28, an avatar-creating unit 39 and optionally a limit-positioning-determining unit 31, all of which are located in the control device 26. As mentioned, instead of being accommodated in the control device 26, the registration unit 27 can also be accommodated in the camera-unit 4 and the optional limit-positioning-determining unit 31 in the limit-positioning-capturing unit 32 or the display unit 5.

Finally, the device according to an embodiment of the invention contains outside the control device 26 a limit-positioning-capturing unit 32 and an image-display unit 33 both of which are accommodated in the display unit 5, which, by way of example, is embodied as a touch-screen monitor 5. The components or assemblies of the device according to the invention are connected to one another in a suitable manner in a signal conducting manner in order to cooperate in accordance with the method. In this case, "in a signal conducting manner" should be understood to mean not only an electrically conducting connection, but also any kind of wireless connection. In particular, the components or assemblies can also be connected to one another via a bus system.

The function of the device according to an embodiment of the invention with the first variant is as follows:

An operator starts the function of the method according to an embodiment of the invention for controlling the positioning of the geometric course of a scanning region 15 of the CT device 8 to a (not shown) console of the CT device 8. First, 2D image data BD of the patient 1 lying on the bed 7 is created by means of 2D camera 41 of the TOF camera 4 and this 2D image data BD is routed via the signal line 36 to the processor 30 of the control unit 26, which optionally reworks this image data BD and, on the one hand, stores it in the registration unit 27 and, on the other, routes it via the output interface 29 to the image-display unit 33 of the display unit 5 where this 2D image data BD is displayed in the form of a 2D image 2 for the operator.

Simultaneously with the 2D image data BD, depth image data TD of the patient 1 lying on the bed 7 is created and this depth image data TD is routed via the signal line 36 to the processor 30 of the control unit 26 where this depth image data TD is then optionally reworked and routed to the registration unit 27. There, the depth image data TD is registered to the stored 2D image data BD registers.

When the display unit 5 is tapped, for example, with a finger of the operator, the limit-positioning-capturing unit 32 captures corresponding limit position data and, to determine a start line 14 and end line 16 of the scanning region 16, optionally routed via the limit-positioning-determining unit 31 to the limit-contour-line-determining unit 28.

The depth image data TD is then routed from the registration unit 27 to the limit-contour-line-determining unit 28, where at least one algorithm virtually reflecting real projected light or laser markings is stored. This algorithm is then used to calculate limit contour line data, here for example in the form of a start line 14 and end line 16, on the basis of the depth image data TD and the limit position data of the limit-positioning-capturing unit 32 which is also routed into the limit-contour-line-determining unit 28 optionally via the limit-positioning-determining unit 31. The operator is able to change the positions of the lines 14, 16 by further tapping the lines 14, 16 and pulling them in the longitudinal direction (z-direction) on the touch display until the operator has finally defined a scanning region 15 between the lines 14, 16 suitable for the subsequent scanning process.

The limit contour line data of the start line 14 and end line 16 of the scanning region 15 can then be used in the conventional way (like the position data of a light sighting device) to control the CT device during the subsequent scan.

With a second variant, following the start, the operator creates the depth image data TD and optionally the 2D image data BD of the patient 1 lying on the bed 7 by means of the TOF camera 4 and routes it to the avatar-creating unit 39, which uses this data to create a three-dimensional avatar 50 of the examination object 1. This is then displayed on the display unit 5.

As described previously for the first variant, here once again by tapping on the display unit 5, for example, with a finger, the operator is able to ensure that corresponding limit position data or limit lines 51, 52, 53, 54 of the scanning region 55, 56 are determined. Here, once again, the operator can change the positions of the limit lines 51, 52, 53, 54 by further tapping on the limit lines 51, 52, 53, 54 and pulling, until the operator has finally defined a scanning region scanning region 55, 56 between the limit lines 51, 52, 53, 54 suitable for the subsequent scanning process. In addition, here can the operator can activate the avatar 50 on the display unit 5 rotate it in any direction.

Reference is made once again to the fact that the method described in detail above and the device shown are only exemplary embodiments, which can be modified by the person skilled in the art in a wide variety of ways without departing from the scope of the invention. Although, the invention was described by way of example for use on a computed tomography system, this does not exclude advantageous use on other medical imaging systems, such as, for example, other X-ray-based systems, for example for the creation of conventional X-ray images or fluoroscopic images;
magnetic resonance imaging devices (MRI) devices;
systems for creating images on the basis of radionuclides, for example scintigraphy, positron emission tomography (PET), single-photon emission computed tomography (SPECT);
systems for creating images on the basis of ultrasound waves, for example sonography, color Doppler;
systems for creating images on the basis of infrared radiation, for example diagnostic thermography;
systems for creating images on the basis of electrical resistances or impedances, for example electrical impedance tomography (EIT);
systems for creating images on the basis of visible light, for example endoscopy, optical tomography.

Furthermore, the examination region can in principle have any shape desired, i.e. in other embodiments, the examination region can be defined on the 2D image of the patient for example as a 2D rectangle or 2D polygon or as a 2D free-form surface instead of by simple start and end lines. Furthermore the use of the indefinite article "a" or "an" does not preclude the possibility that the features in question may also be present on a multiple basis. Similarly, the term "unit" and "module" does not preclude the possibility of the unit comprising a plurality of components, which could also be spatially distributed.

The invention claimed is:

1. A method of determining a scanning region of a medical imaging system usable for recording of a region of interest of an examination object, comprising:
    capturing depth image data of the examination object;
    creating 2D image data of at least one 2D image of the examination object;
    registering the created 2D image data and the captured depth image data of the examination object to each other, at least in some regions;
    determining first start and stop lines representing a region of the examination object to be scanned by the medical imaging system;
    displaying the 2D image and, using the 2D image, determining at least one limit position of the scanning region;
    determining at least one corrected start and stop line representing a corrected region of the examination object to be scanned by the medical imaging system as at least one limit contour line, extending through the at least one limit position, on the basis of the captured depth image data of the examination object registered to the 2D image data and the at least one determined limit position in the 2D image of the examination object; and
    superimposing the determined at least one limit contour line on the displayed 2D image of the examination object.

2. The method of claim 1, further comprising:
    determining biometric data of the examination object on the basis of the 2D image data and creating an avatar for the examination object based on said biometric data.

3. The method of claim 1, wherein the limit contour line corresponds to a light or laser marking projected virtually onto the displayed 2D image of the examination object.

4. The method of claim 2, wherein at least two limit lines of a scanning region of the avatar are displayed in the form of at least one start line and at least one end line between which the scanning region is defined.

5. The method of claim 1, wherein the 2D image data of the examination object is captured in visible wavelength range and the 2D image displayed as a color image.

6. The method of claim 1, wherein the depth image data of the examination object is captured in the infrared wavelength range.

7. The method of claim 1, wherein the 2D image data and the depth image data of the examination object are captured from the same perspective.

8. The method of claim 1, wherein at least one of the 2D image data and the depth image data of the examination object are captured from a position, located approximately over at least one of a geometric center of a planned, envisaged scanning region and in a region over a geometric center of an object table on which the examination object is arranged.

9. The method of claim 1, wherein the 2D image data and the depth image data of the examination object are created simultaneously or at approximately the same time.

10. The method of claim 1, wherein the 2D image and the at least one limit contour line are displayed on a display unit comprising an image-display unit and a line-positioning-capturing unit.

11. The method of claim 10, wherein the line-positioning-capturing unit of the display unit is configured to detect movements of a pointer object and wherein the at least one limit contour line is changed synchronously with a movement of a pointer object relative to the 2D image displayed on the image-display unit.

12. A medical imaging system for recording of a region of interest of an examination object, the medical imaging system comprising:
    a depth-image-data sensor configured to capture depth image data of the examination object;
    a 2D camera configured to create 2D image data of at least one 2D image of the examination object;
    a registration unit configured to register the 2D image data to the depth image data of the examination object at least in some regions;
    a determining unit configured to determine first start and stop lines representing a region of the examination object to be scanned by the medical imaging system; and an avatar-creating unit configured to create a three-dimensional avatar of the examination object on the basis of the depth image data registered to the 2D image data of the examination object;

an image-display unit to display at least one of the 2D image and the avatar of the examination object;

a limit-positioning-capturing unit configured to capture at least one limit position of the scanning region by using at least one of the 2D image and the avatar displayed; and a limit-contour-line-determining unit configured to determine a limit contour line of the scanning region representing a corrected scanning region extending through the limit position on the basis of the depth image data and the limit position of the scanning region in the 2D image, said limit contour line being displayed superimposed on the 2D image in the image-display unit.

13. The medical imaging system of claim 12, wherein the 2D camera and the depth-image-data sensor are combined to form a camera unit.

14. The medical imaging system of claim 12, wherein the image-display unit and the line-positioning-capturing unit are combined in a display unit.

15. The method of claim 4, wherein at least two limit contour lines extend transversely to a direction of movement of an object table on which the examination object is arrangeable.

16. The method of claim 11, wherein the at least one limit contour line is displaced in a direction of movement of an object table on which the examination object is arranged.

17. The medical imaging system of claim 12, wherein the 2D camera, the depth-image-data sensor and the registration unit are combined to form a camera unit.

18. The medical imaging system of claim 13, wherein the image-display unit and a line-positioning-capturing unit are combined in a display unit.

19. The medical imaging system of claim 12, wherein the image-display unit and a line-positioning-capturing unit are combined in a touch-screen monitor.

20. The medical imaging system of claim 13, wherein the image-display unit and a line-positioning-capturing unit are combined in a touch-screen monitor.

21. A computed tomography device, comprising the device of claim 12.

* * * * *